(12) United States Patent
Pierson

(10) Patent No.: US 6,245,071 B1
(45) Date of Patent: Jun. 12, 2001

(54) EXTERNAL FIXATION DEVICE FOR BONE

(75) Inventor: Glen J. Pierson, Glenmoore, PA (US)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/265,584

(22) Filed: Mar. 10, 1999

(51) Int. Cl.$^7$ .................................................. A61B 17/60
(52) U.S. Cl. .................................................. 606/58; 606/57
(58) Field of Search ........................... 606/53–58, 60–64, 606/87, 96, 105; 128/92

(56) References Cited

U.S. PATENT DOCUMENTS

| Re. 34,985 | 6/1995 | Pennig ........................... 606/58 |
| 4,040,129 | * 8/1977 | Steinemann et al. ............. 128/92 |
| 4,554,915 | 11/1985 | Brumfield ....................... 128/92 A |
| 4,611,586 | 9/1986 | Agee et al. ..................... 128/92 A |
| 4,628,919 | 12/1986 | Clyburn ......................... 128/92 ZK |
| 4,662,365 | 5/1987 | Gotzen et al. .................. 128/92 ZW |
| 4,782,842 | 11/1988 | Fietti, Jr. ........................ 128/92 Z |
| 4,919,119 | 4/1990 | Jonsson et al. .................. 606/54 |
| 4,922,896 | 5/1990 | Agee et al. ..................... 606/55 |
| 4,978,348 | 12/1990 | Ilizarov .......................... 606/57 |
| 4,988,349 | 1/1991 | Pennig ........................... 606/58 |
| 5,122,140 | 6/1992 | Asche et al. .................... 606/55 |
| 5,152,280 | 10/1992 | Danieli .......................... 128/54 |
| 5,207,676 | 5/1993 | Canadell et al. ................. 606/54 |
| 5,304,177 | 4/1994 | Pennig ........................... 606/58 |
| 5,320,622 | 6/1994 | Faccioli et al. .................. 606/58 |
| 5,376,091 | * 12/1994 | Hotchkiss et al. ............... 606/55 |
| 5,437,667 | 8/1995 | Papierski et al. ................. 606/55 |
| 5,545,162 | 8/1996 | Huebner .......................... 606/57 |
| 5,601,551 | 2/1997 | Taylor et al. ..................... 606/54 |
| 5,662,649 | 9/1997 | Huebner .......................... 606/57 |
| 5,683,389 | 11/1997 | Orsak ............................. 606/59 |
| 5,743,898 | 4/1998 | Bailey et al. .................... 606/54 |
| 5,843,081 | * 12/1998 | Richardson ...................... 606/58 |
| 6,033,412 | * 3/2000 | Losken et al. ................... 606/105 |

FOREIGN PATENT DOCUMENTS 8802-462-A   5/1990   (NL) .

* cited by examiner

Primary Examiner—Cary O'Connor
(74) Attorney, Agent, or Firm—Pennie & Edmonds LLP

(57) ABSTRACT

The present invention is directed to a device for fixation of a bone fracture. The device comprises at least one distal pin having a mounting end for insertion on a distal side of the fracture, at least one proximal pin having a mounting end for insertion on a proximal side of the fracture, a distal member attached to the distal pins, a proximal member attached to the proximal pins and slideably connected to the distal member for reducing or distracting the bone fracture, a distraction assembly for controlling the movement between the proximal and distal members, and a removable engagement element. The distraction assembly has two modes of operation: an active configuration and an inactive configuration. In the active configuration, incremental relative sliding movement between the proximal and distal members is allowed, and, in the inactive configuration, free relative sliding movement between the proximal and distal members is allowed. The engagement element operatively engages the distraction assembly in the inactive configuration. Removal of the engagement element places the distraction assembly in the active configuration.

25 Claims, 8 Drawing Sheets

EXTERNAL FIXATION DEVICE FOR BONE

FIELD OF THE INVENTION

The present invention relates to a device for fixation of bone, and in particular to an external fixation device for a long bone.

BACKGROUND OF THE INVENTION

The clinical success of external fixation of bones has been well documented in the orthopaedic literature. However, external fixation at or near a joint can be problematic due to biomechanical requirements. For example, because the wrist has degrees of freedom which allow rotation, flexion, adduction, and abduction, external fixation near the wrist should be adjustable to ensure that proper fracture alignment is achieved. Furthermore, in order to avoid damage to the tendons and nerves that surround the wrist, the pins which are used to couple the fixation device to the body are usually placed on opposite sides of the wrist in the metacarpal bone and the radius. As a result, the fixation device must be sufficiently articulated to reduce the fracture using the forces transmitted through the wrist.

In order to address these, as well as other complications associated with fixation at or near a joint, a number of fixation devices have been developed. Examples include those disclosed in U.S. Pat. Nos. 4,554,915, 4,611,586, 4,628,919, 4,782,842, 4,919,119, 4,922,896, Re. 34,985, 5,122,140, 5,152,280, 5,304,177, 5,320,622, 5,437,667, 5,545,162, 5,601,551, 5,683,389, and 5,743,898. One particular problem common to these, as well as other prior art devices, is the need to have both large scale distraction to facilitate implantation and precisely controlled distraction to ensure proper fracture reduction. Some of these patents attempt to overcome this dilemma by requiring assembly and/or disassembly of multiple parts. U.S. Pat. No. 5,662,649 to Huebner discloses an external fixator for repairing fractures of the distal radius and wrist which allows both rapid gross distraction and finely controlled distraction without the need for intraoperative assembly or disassembly. However, the nut and thread assembly which permits both types of movement can be cumbersome to use and unintentional switching between the movement modes is possible.

As the discussion above illustrates, there is a need for an improved external fixation device for bone.

SUMMARY OF THE INVENTION

The present invention relates to a device for fixation of a bone fracture. The device comprises at least one distal pin having a mounting end for insertion into the bone on a distal side of the fracture, at least one proximal pin having a mounting end for insertion into the bone on a proximal side of the fracture, a distal member attached to the distal pins, a proximal member attached to the proximal pins and slideably connected to the distal member for reducing or distracting the bone fracture, and a distraction assembly for controlling the sliding movement between the proximal and distal members. The distraction assembly has two modes of operation: an active configuration and an inactive configuration. In the active configuration, incremental relative sliding movement between the proximal and distal members is allowed, and, in the inactive configuration, free relative sliding movement between the proximal and distal members is allowed. The free sliding movement is useful in installation of the device and the incremental relative sliding movement is useful for finely manipulating the relative positions of the proximal and distal members.

The device also includes a removable engagement element operatively engaging the distraction assembly in the inactive configuration. Removal of the engagement element places the distraction assembly in the active configuration. Once the engagement element is removed, it cannot easily be replaced. As a result, the distraction assembly cannot inadvertently be placed in the inactive configuration.

Preferably, the distraction assembly comprises a gear rack on a wall of the proximal member body cavity, an intermediate gear engageable with the gear rack to cause the incremental relative sliding movement between the proximal and distal members upon rotation of the intermediate gear, a worm gear engageable with the intermediate gear so that rotation of the worm gear causes rotation of the intermediate gear, and a resilient member which biases the worm gear into engagement with the intermediate gear. The removable engagement element may be a pin located between the intermediate gear and the worm gear to prevent engagement between the intermediate gear and the worm gear.

In one embodiment, the device also includes a distal mounting blocks for attaching the distal pins to the distal member and a proximal mounting block for attaching the proximal pins to the proximal member. Each pin, which may be Schanz screws or any other suitable fastener, fits into a channel in the proximal and distal mounting blocks and a locking screw secures the respective pin to the channel. In order to avoid interference with anatomical structures, the channel may be oriented at an angle of about 45° with respect to the longitudinal axis of the device.

In a preferred embodiment, at least one of the distal and proximal mounting blocks includes a ball joint for allowing rotational movement of the mounting blocks with respect to the rest of the device. The distal and proximal mounting blocks may include a plurality of set screws for securing the mounting blocks at a desired position with respect to the proximal and distal members. In a further preferred embodiment, two set screws oriented perpendicular to each other are used for each ball joint.

In a different embodiment, the distal mounting block has an arm for connection with the distal member and the distal member has a head with a track for receiving the arm. The arm is movable in the track to vary the position of the distal mounting block with respect to the distal member. The track may be curved with teeth which engage a gear on the arm upon rotation of the gear to move the distal mounting block. Preferably, a locking element is provided to prevent rotation of the gear and fix the position of the distal mounting block.

In order to have the sliding movement between the proximal and distal members, the proximal member may include a body and a linking section. The body has a cavity for slideably receiving the distal member. In addition, the linking section may be slideably connected to the body so that sliding motion between the linking section and the body occurs in a direction perpendicular to the direction of the sliding motion between the proximal and distal members. The sliding motion between the linking section and the body is coplanar to the sliding motion between the proximal and distal members. In a preferred embodiment, a distal end of the linking section includes a pair of slots and the proximal end of the body includes a cutout. The cutout slides in the slots to produce the sliding motion between the linking section and the body. In a further preferred embodiment, a lead screw connects the linking section to the body. Turning of the lead screw moves the linking section relative to the body.

In another embodiment, the proximal member has a tail pivotably connected to the linking section. The tail has a worm gear and the linking section has a curved gear rack. The worm gear engaging the gear rack to produce the pivotal movement between the tail and the linking section.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
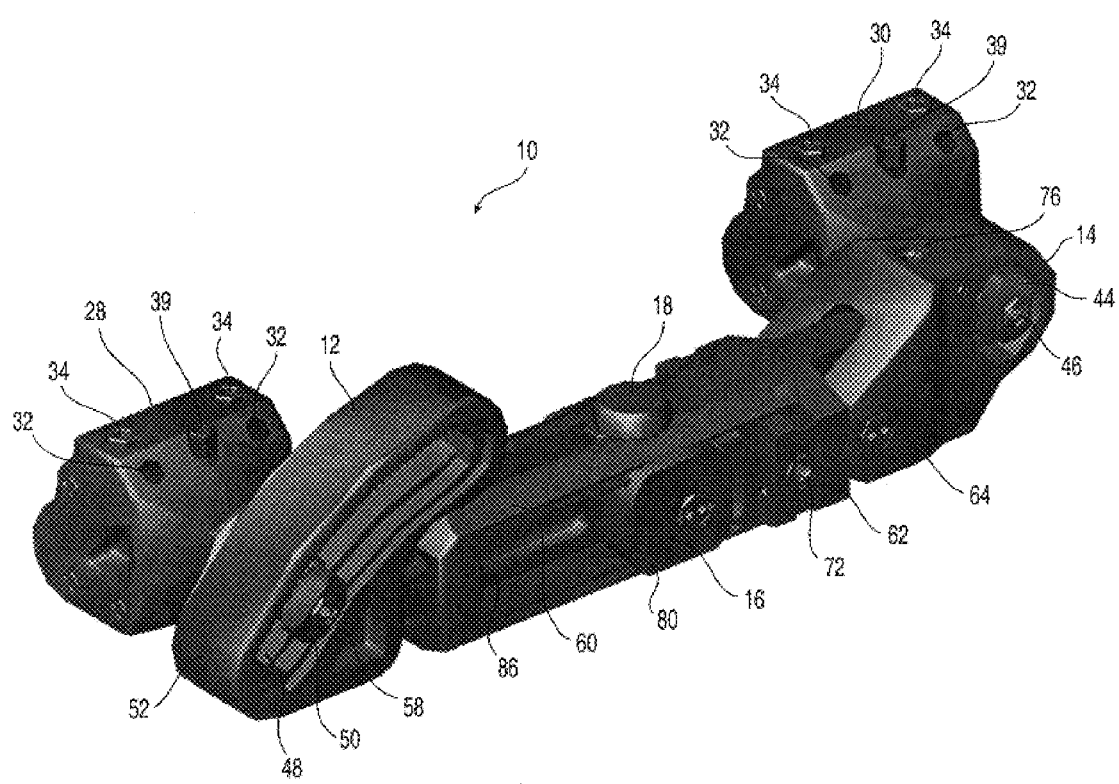
FIG. 1 shows a perspective view of an external fixation device according to the present invention from the left side.
Figure 2:
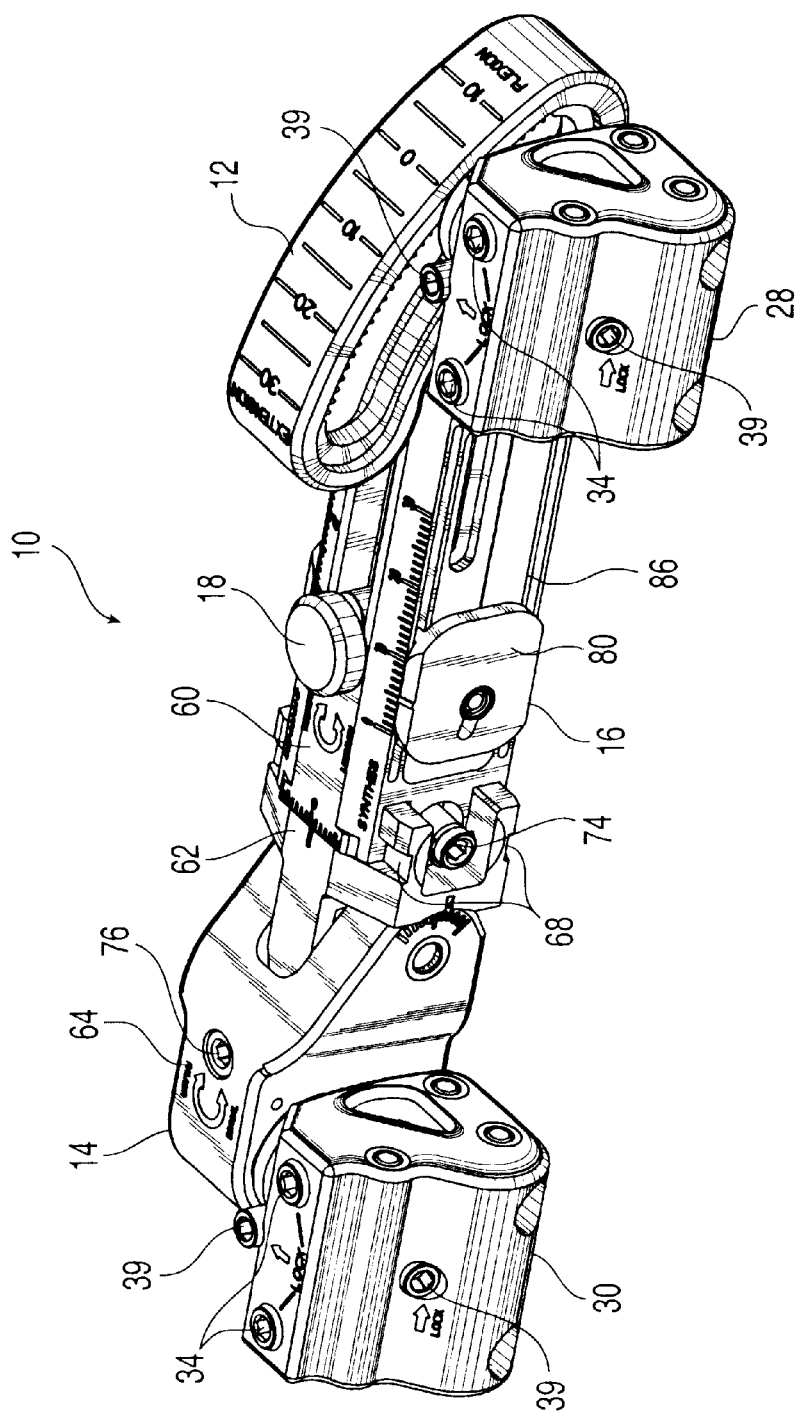
FIG. 2 shows a perspective view of the device from the right side.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto. Finally, any reference to a particular biological application, such as fixation at or near the wrist, is simply used for convenience as one example of a possible use for the invention and is not intended to limit the scope of the present invention thereto.

Referring to FIGS. 1–4, an external fixation device or fixator 10 according to the present invention includes a distal member 12, a proximal member 14 slideably connected to distal member 12, and a distraction assembly 16 for controlling the sliding movement between proximal and distal members 12, 14, and a removable engagement element 18. Thus, as used in this application, the term distal designates the end or direction near distal member 12 of fixator 10, and the term proximal designates the end or direction near proximal member 14 of fixator 10. Most components of fixator 10 are made of radiolucent plastic or composite materials to minimize the radiographic interference of fixator 10. As will be described in more detail later, distal member 12 is joined to the bone on one side of the bone fracture and proximal member 14 is joined to the bone of the other side of the bone fracture. Thus, the sliding movement between distal and proximal members 12, 14 results in reduction or distraction of the bone fracture. As will also be described in more detail later, distraction assembly 16 has an active configuration in which only incremental relative sliding movement between distal and proximal members 12, 14 is possible and an inactive configuration in which free relative sliding motion between distal and proximal members 12, 14 is possible. The incremental sliding motion is needed to finely control distraction and reduction and the free sliding motion is useful to facilitate installation and preoperative setup of fixator 10. As will also be described in more detail below, engagement element 18 operatively engages distraction assembly 16 in the inactive configuration so that free sliding motion between distal and proximal members 12, 14 is ordinarily possible. However, upon removal of engagement element 18, distraction assembly is placed in the active configuration to limit the sliding motion between distal and proximal members 12, 14 to incremental sliding motion.

Figure 8:
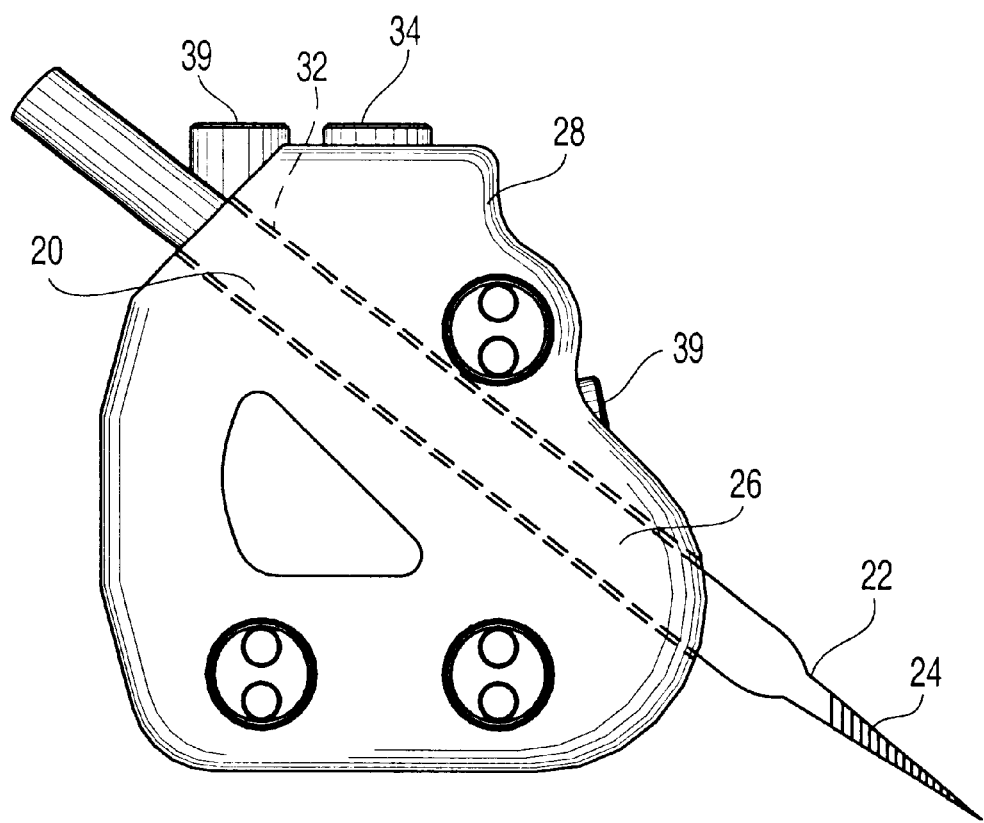
FIG. 8 shows a side view of one embodiment of a pin for coupling the device to bone.

FIG. 8 shows one embodiment of a pin 20 for coupling fixator 10 to bone. Although pin 20 is shown and described as a fastener commonly referred to as a Schanz screw, any number of known fastening devices can be used to secure fixator 10 to bone. Pin 20 has a tapered mounting end 22 with threads 24 for engaging the bone and a shaft 26. At least one pin 20 is used to couple distal member 12 to the distal side of the bone fracture and at least one pin 20 is used to couple proximal member 14 to the proximal side of the bone fracture. Preferably, two pins 20 are used for distal member 12 and two pins 20 are used for proximal member 14. Distal pins 20 are connected to distal member 12 by distal mounting block 28 and proximal pins 20 are connected to proximal member 14 by proximal mounting block 30. Distal and proximal mounting blocks 28, 30 include a plurality of channels 32 for pins 20. Channels 32 are preferably oriented obliquely at an angle of about 45° with respect to the longitudinal axis of fixator 10 to avoid interference with anatomical structures and provide for improved x-ray visibility in lateral views. This orientation is particularly useful if fixator 10 is used near the wrist to minimize hindrance with the thumb. A locking screw 34 locks pin 20 to channel 32.

Figure 4:
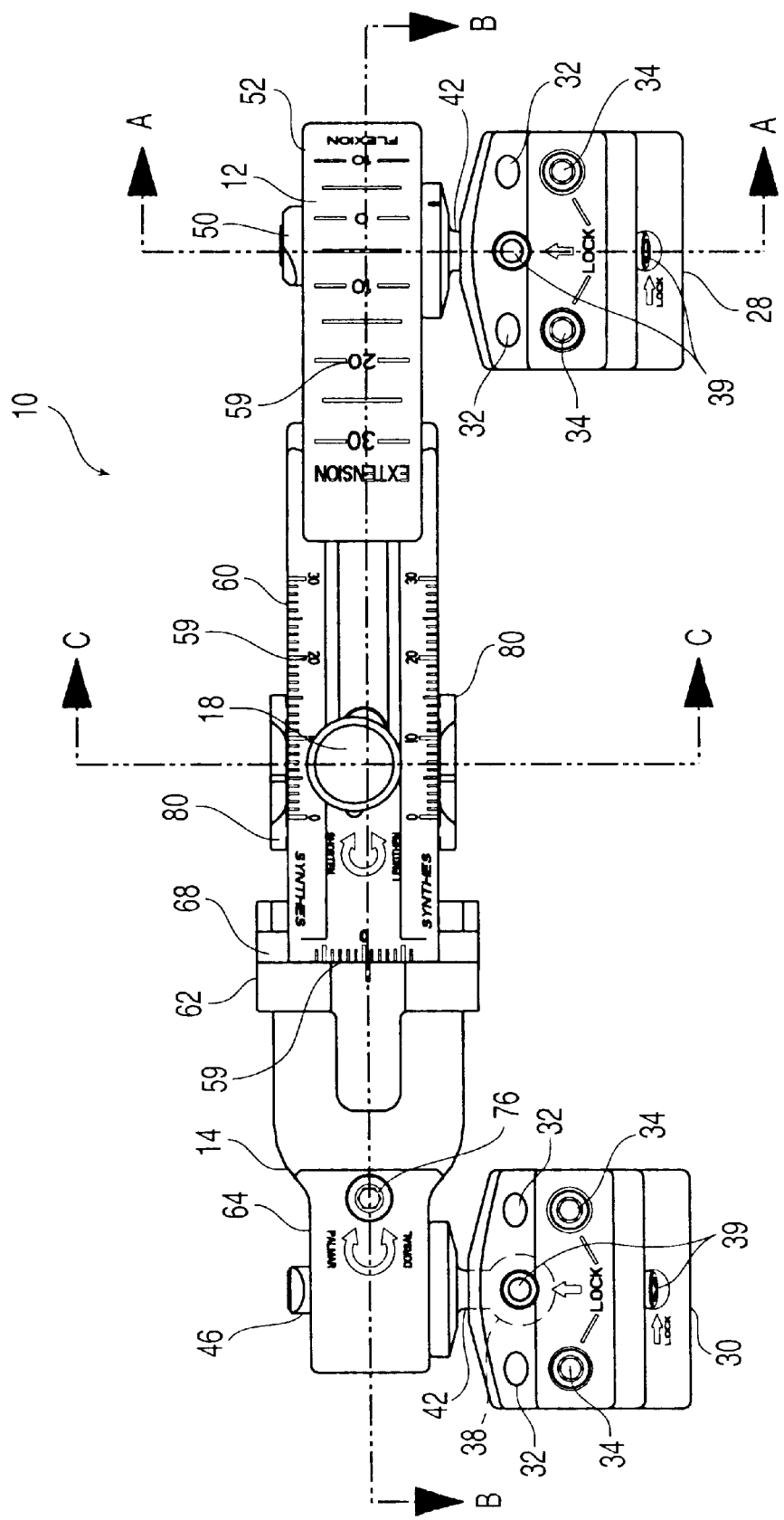
FIG. 4 shows a top view of the device.
Figure 5:
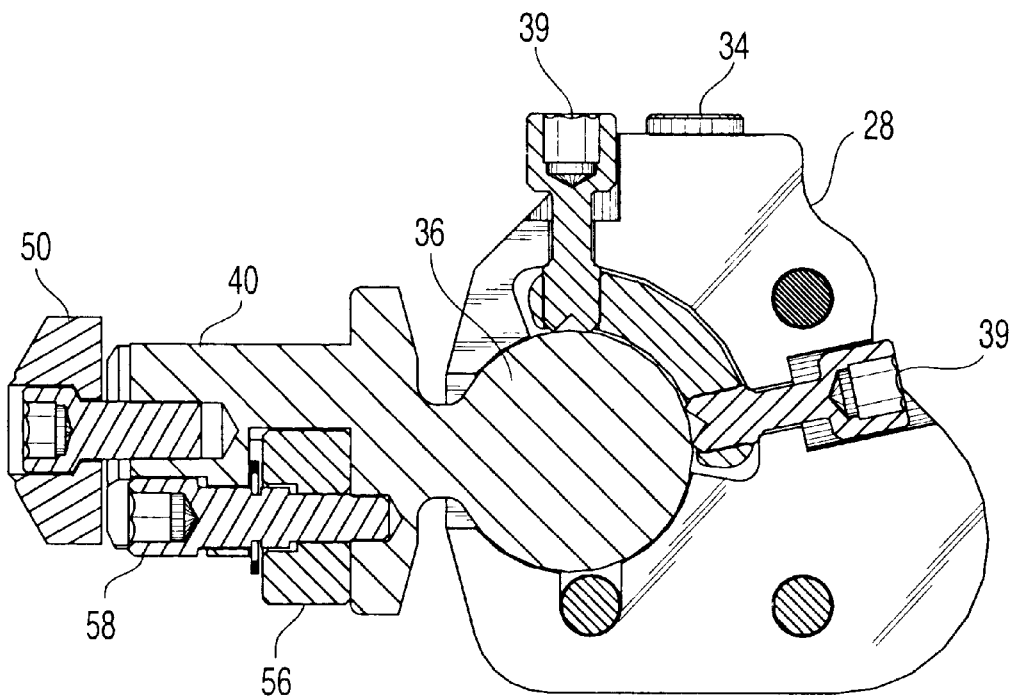
FIG. 5 is a sectional view taken along line A—A of FIG. 4 showing the ball joint of the distal mounting block.

As best seen in FIGS. 4 and 5, distal and proximal mounting blocks 28, 30 include ball joints 36, 38 respectively. As ball joints 36, 38 provide one rotational degree of freedom and two pivotal degrees of freedom, a wide range of articulations is possible with respect to the orientation of distal and proximal mounting blocks 28 to distal and proximal members 12, 14. This facilitates application of fixator 10. Specifically, a template is typically used to insert the pins on both sides of the fracture, i.e. the proximal and distal pins and then the external fixation device is linked to the pins. In prior art devices, the placement of the pins was crucial to ensure that the external fixation device was properly aligned with the pins. With fixator 10, the placement of pins 20 is not as critical because of the wide range of motion provided by ball joints 36, 38.

It should be noted that ball joints are optional and, if used, can be used on either one or both of distal and proximal mounting blocks 28, 30. However, for simplicity, this description will assume that both ball joints 36, 38 are used. Once the desired orientation of distal mounting block 28 with respect to distal member 12 has been achieved, a set screw 39 locks the two at the desired orientation. Although only one set screw 39 is needed to fix ball joint 36, preferably two set screws 39 are present. In a further preferred embodiment, these two set screws are perpendicular to each other so that if one set screw is loosened, some movement of ball joint 36 is possible without permitting totally free movement. This is particularly useful in fine tuning the orientation of mounting blocks 28, 30 with respect to members 12, 14.

Figure 3:
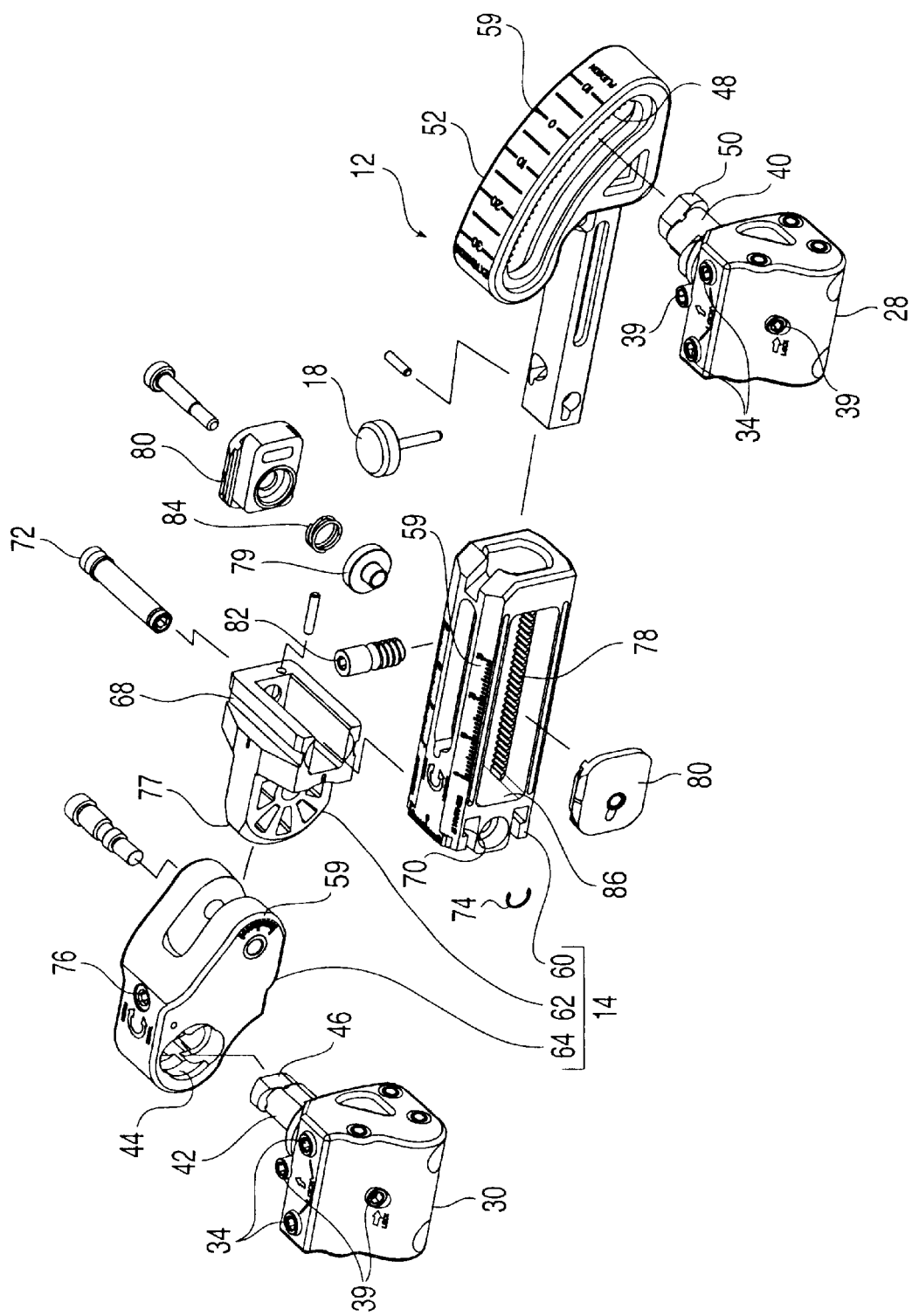
FIG. 3 shows an exploded view of the device with scales added to provide indicia as to relative movement between two components.

FIGS. 1, 3, and 4 show that a distal arm 40 is located medial to distal ball joint 36 for connecting distal mounting block 28 to distal member 12. Similarly, a proximal arm 42 is located medial to proximal ball joint 38 for connecting proximal mounting block 30 to proximal member 14. Proximal arm 42 fits into a hole 44 on proximal member 14 and a nut member 46 secures arm 42 to proximal member 14. Distal arm 40 fits into an elongated hole or track 48 on distal member 12 and a nut member 50 secures arm 40 to distal member 12. Because nut members 46, 50 can be loosened and fixator 10 has substantial lateral symmetry, distal and proximal mounting block 28, 30 can be placed on either side of fixator 10. As a result, fixator 10 can be used on the left or the right side of the body and placed on the lateral or medial side of the bone as required by a particular clinical application.

Figure 6:
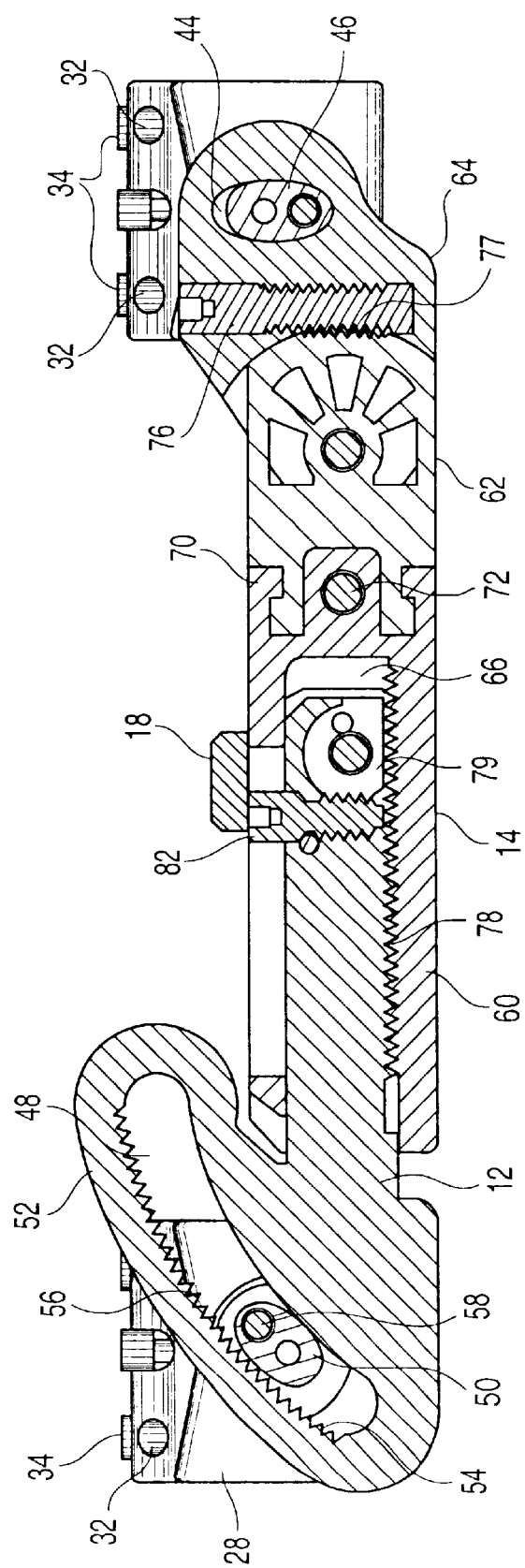
FIG. 6 is a sectional view taken along line B—B of FIG. 4 showing the entire fixator.

Elongated hole 48 is located in a head portion 52 of distal member 12. When distal nut member 50 is not tightened, distal arm can move along elongated hole 48 to vary the position of distal mounting block 28 with respect to distal member 12. Preferably, elongated hole 48 has a curved arc shape. This is particularly useful if fixator 10 is used near the wrist so that flexion and extension movement of the hand is permitted. In order to control the flexion and extension movement, elongated hole 48 has teeth 54 that cooperate with an arm gear 56 on distal arm 40 (FIG. 6). By turning a first adjustment screw 58, gear 56 turns to move along teeth 54. Distal nut member 50 functions as a locking element by preventing rotation of gear 56 and thereby fixing the position of distal mounting block 28. A scale 59 provides indicia as to the relative movement between distal mounting block 28 and distal member 12 (FIGS. 3 and 4). In order to minimize gear backlash, gear 56 can be made of metal and teeth 54 can be made of plastic.

Referring primarily to FIGS. 3, 4, and 6, proximal member 14 includes a body 60, a linking section 62, and a tail 64. Body 60 has a cavity 66 for slideably receiving distal member 12. Linking section 62 is slideably connected to body 60 in such a fashion that the sliding motion between linking section 62 and body 60 occurs in a direction perpendicular to the direction of the sliding motion between distal and proximal members 12, 14. As these two sliding motions are also coplanar, if fixator 10 is used in the area near the wrist, the sliding motion between linking section 62 and body 60 is in the medial-lateral anatomical direction. A distal end of linking section 62 includes a pair of slots 68 slots and a proximal end of body 60 includes a cutout 70 which is slideable in slots 68 to thereby produce the sliding motion between body 60 and linking section 62. A lead screw or second adjustment screw 72 connects linking section 62 to body 60 so that turning of lead screw 72 moves linking section 62 relative to body 60. A washer 74 limits the total amount that lead screw 72 can be rotated to prevent movement of cutout 70 out of slots 68.

Tail 64 is pivotably connected to linking section 62. Thus, if fixator 10 is used near the wrist, palmar and dorsal movement of the hand is permitted. A worm gear or third adjustment screw 76 on tail 64 cooperates with a curved gear rack 77 on linking section 62 to control the movement between linking section 62 and tail 64. By turning worm gear 76, the position of linking section 62 relative to tail 64 can be adjusted. A scale 59 provides indicia as to the relative movement between tail 64 and linking section 62 (FIGS. 3 and 4). In order to minimize gear backlash, worm gear 76 can be made of metal and gear rack 77 can be made of plastic.

Figure 7:
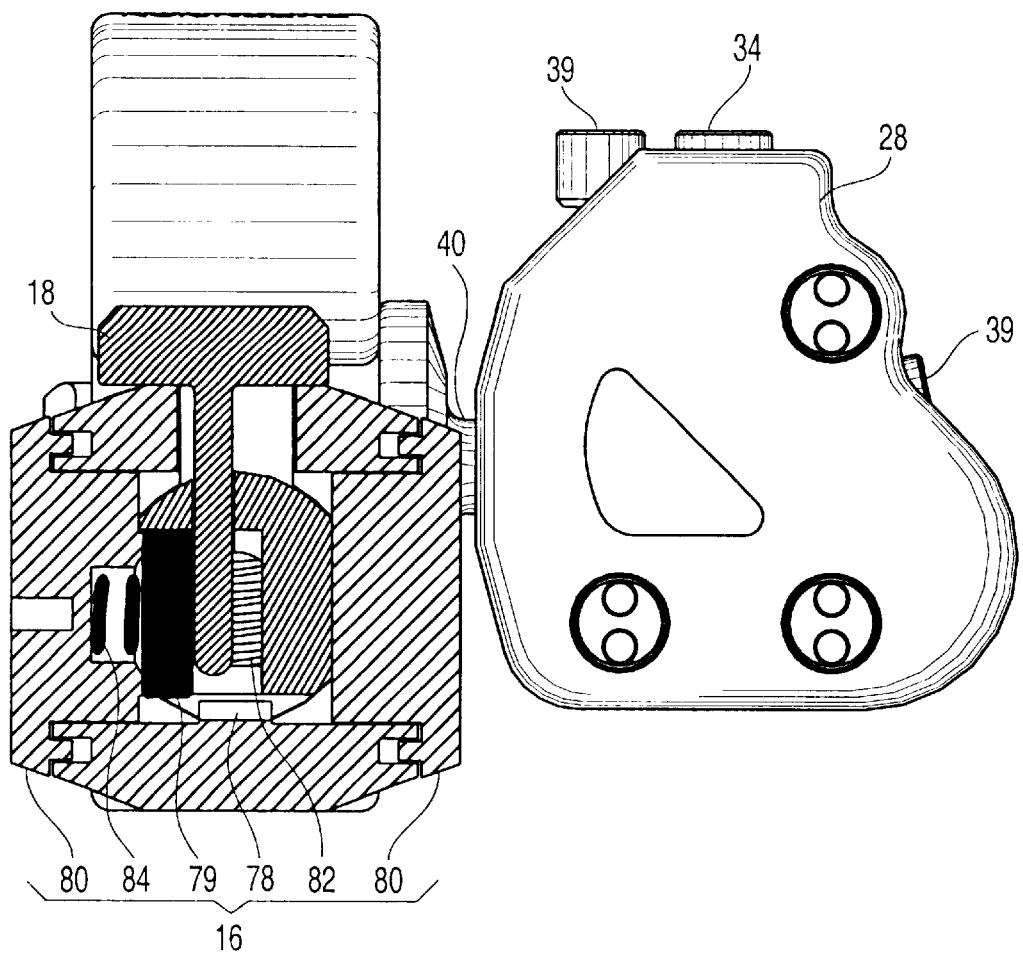
FIG. 7 is a sectional view taken along line C—C of FIG. 4 showing a portion of the distraction assembly.

As previously discussed, distraction assembly 16 controls the sliding motion between distal and proximal members 12, 14. The sliding motion results in a reduction or increase in distance between distal member 12 and proximal member 14. Referring primarily to FIGS. 3, 6, and 7, distraction assembly 16 includes a gear rack 78 located on a wall of cavity 66. An intermediate gear 79 is engageable with gear rack 78. A scale 59 provides indicia as to the relative movement between distal and proximal members 12, 14 (FIGS. 3 and 4). In order to minimize gear backlash, intermediate gear 79 can be made of metal and gear rack 78 can be made of plastic. As intermediate gear 79 is connected to distal member 12 via distraction assembly side members 80, movement of intermediate gear 79 along gear rack 78 causes incremental relative sliding movement between distal and proximal members 12, 14. When only incremental motion between distal and proximal members 12, 14 is possible, distraction assembly 16 is in the active configuration. A worm gear or fourth adjustment screw 82 is engageable with intermediate gear 79 so that rotation of worm gear 82 causes rotation of intermediate gear 79. But for the presence of engagement element 18 located between intermediate and worm gears 79, 82, a resilient member 84, such as a coil spring, would bias worm gear 82 into engagement with intermediate gear 79. With engagement element 18 located between intermediate and worm gears 79, 82, distraction assembly 16 is in the inactive configuration and distal and proximal members 12, 14 can freely slide relative to one another. In addition to serving as part of the coupling mechanism between distal and proximal members 12, 14 and keeping the various elements of distraction assembly 16 in proper relationship to each other as distraction assembly 16 moves, interference between side members 80 and the ends of window 86 on body 60 limits the total possible movement of distal member 12 with respect to proximal member 14.

In order to cause engagement between intermediate and worm gears 79, 82 and thereby place distraction assembly 16 in the active configuration from the inactive configuration, i.e. change the sliding movement between distal and proximal members 12, 14 from gear-independent free sliding movement to gear-driven incremental sliding movement, engagement element 18 is simply removed to allow resilient member 84 to push the teeth of intermediate gear 79 into engagement with the teeth of gear rack 78 and worm gear 82. Preferably, engagement element 18 is a pin with a head having knurling for ease of handling. Once engagement element 18 is removed, it cannot be easily put back into place because of interference by resilient member 84. Thus, distraction assembly 16 cannot inadvertently be placed back into the inactive configuration once engagement element 18 is removed. In order to replace engagement element 18, a specially designed tool is needed to counter act the biasing force of resilient member 84 and disengage intermediate gear 79 from gear rack 78 and worm gear 82. As a result, it is extremely difficult to place distraction assembly into the inactive configuration without this tool.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A device for fixation of a bone fracture comprising:
   at least one distal pin having a mounting end for insertion into the bone on a distal side of the fracture;
   at least one proximal pin having a mounting end for insertion into the bone on a proximal side of the fracture;
   a distal member attached to the at least one distal pin;
   a proximal member attached to the at least one proximal pin and slidably connected to the distal member for reducing or distracting the bone fracture;
   a distraction assembly having an active configuration and an inactive configuration, and operatively associated with the distal and proximal members in both the active and inactive configurations, with the active configuration allowing incremental geared relative movement between the proximal and distal members and the inactive configuration allowing a continuum of free relative sliding movement between the proximal and distal members; and
   a removable engagement element operatively engaging the distraction assembly in the inactive configuration, wherein removal of the engagement element places the distraction assembly in the active configuration.

2. The device of claim 1 further comprising:
   a distal mounting block for attaching the at least one distal pin to the distal member; and
   a proximal mounting block for attaching the at least one proximal pin to the proximal member.

3. The device of claim 2 wherein the at least one proximal and distal pins are Schanz screws.

4. The device of claim 2 wherein the proximal and distal mounting blocks include a channel for each of the at least one proximal and distal pins.

5. The device of claim 4 wherein each channel has a locking screw for securing the respective pin to the channel.

6. The device of claim 4 wherein the channel is oriented at an angle of about 45° with respect to the longitudinal axis of the device for avoiding interference with anatomical structures.

7. The device of claim 2 wherein at least one of the distal and proximal mounting blocks includes a ball joint for allowing rotational movement.

8. The device of claim 7 wherein at least one of the distal and proximal mounting blocks includes a plurality of set screws for securing the at least one of the distal and proximal mounting blocks at a desired position with respect to the proximal and distal members.

9. The device of claim 8 wherein two set screws are provided oriented perpendicular to each other.

10. The device of claim 2 wherein the distal mounting block has an arm for connection with the distal member and the distal member has a head with a track for receiving the arm, the arm movable in the track to vary position of the distal mounting block with respect to the distal member.

11. The device of claim 10 wherein the track is curved.

12. The device of claim 11 wherein the track includes teeth and the arm includes a gear which engages the teeth upon rotation to move the distal mounting block.

13. The device of claim 12 further comprising a locking element for preventing rotation of the gear and thereby fix the position of the distal mounting block.

14. The device of claim 1 wherein the proximal member includes a body and a linking section, the body having a cavity for slideably receiving the distal member.

15. The device of claim 14 wherein the linking section is slideably connected to the body and sliding motion between the linking section and the body occurs in a direction perpendicular to the direction of the sliding motion between the proximal and distal members and the sliding motion between the linking section and the body is coplanar to the sliding motion between the proximal and distal members.

16. The device of claim 15 wherein a distal end of the linking section includes a pair of slots and the proximal end of the body includes a cutout, the cutout sliding in the slots thereby producing the sliding motion between the linking section and the body.

17. The device of claim 16 wherein a lead screw connects the linking section to the body, whereby turning of the lead screw moves the linking section relative to the body.

18. The device of claim 14 wherein the proximal member has a tail pivotably connected to the linking section.

19. The device of claim 18 wherein the tail has a worm gear and the linking section has a curved gear rack, the worm gear engaging the gear rack to produce the pivotal movement between the tail and the linking section.

20. The device of claim 14 wherein the distraction assembly comprises:
    a gear rack on a wall of the proximal member body cavity;
    an intermediate gear engageable with the gear rack to cause the incremental relative sliding movement between the proximal and distal members upon rotation of the intermediate gear;
    a worm gear engageable with the intermediate gear so that rotation of the worm gear causes rotation of the intermediate gear; and
    a resilient member which biases the worm gear into engagement with the intermediate gear.

21. The device of claim 20 wherein the removable engagement element comprises a pin located between the intermediate gear and the worm gear to prevent engagement between the intermediate gear and the worm gear.

22. The device of claim 1 further comprising a resilient member biasing the distraction assembly in the active configuration.

23. A device for fixation of a bone fracture comprising:
    at least one distal pin having a mounting end for insertion into the bone on a distal side of the fracture;
    at least one proximal pin having a mounting end for insertion into the bone on a proximal side of the fracture;
    a distal member attached to the at least one distal pin;
    a proximal member attached to the at least one proximal pin and slidably connected to the distal member for reducing or distracting the bone fracture;
    a distraction assembly having an active configuration and an inactive configuration, and operatively associated with the distal and proximal members in both the active and inactive configurations, with the active configuration allowing incremental relative sliding movement between the proximal and distal members and the inactive configuration allowing free relative sliding movement between the proximal and distal members;
    a resilient member biasing the distraction assembly in the active configuration, and
    a removable engagement element operatively engaging the distraction assembly in the inactive configuration and operatively associated with a blocking member which prevents re-insertion of the engagement element after removal, wherein removal of the engagement element places the distraction assembly in the active configuration.

24. The device of claim 23 wherein removal of the engagement element releases the resilient member to thereby move the blocking member and place the distraction assembly in the active configuration.

25. The device of claim 24 wherein the blocking member is a gear.

\* \* \* \* \*